(12) United States Patent
Lindberg et al.

(10) Patent No.: US 8,009,894 B2
(45) Date of Patent: Aug. 30, 2011

(54) METHOD AND APPARATUS FOR ANALYSIS OF PARTICLES IN A LIQUID SAMPLE

(75) Inventors: Stellan Lindberg, Förslöv (SE); Tom Olesen, Görlöse (DE); Martin Valvik, Hilleröd (DE)

(73) Assignee: Hemocue AB, Angelholm (SE)

( * ) Notice: Subject to any disclaimer, the term of this patent is extended or adjusted under 35 U.S.C. 154(b) by 498 days.

(21) Appl. No.: 12/314,759

(22) Filed: Dec. 16, 2008

(65) Prior Publication Data
US 2009/0185714 A1    Jul. 23, 2009

Related U.S. Application Data

(60) Provisional application No. 61/064,380, filed on Feb. 29, 2008.

(30) Foreign Application Priority Data

Jan. 18, 2008  (SE) ...................................... 0800117

(51) Int. Cl.
*G06K 9/00* (2006.01)
(52) U.S. Cl. ....................................................... 382/141
(58) Field of Classification Search ........................ None
See application file for complete search history.

(56) References Cited

U.S. PATENT DOCUMENTS

| | | | |
|---|---|---|---|
| 5,262,302 A | 11/1993 | Russell | |
| 6,459,473 B1 | 10/2002 | Chang et al. | |
| 6,498,645 B1 * | 12/2002 | Knapp et al. | 356/427 |
| 7,068,365 B2 * | 6/2006 | Hansen et al. | 356/246 |
| 2002/0177885 A1 | 11/2002 | Eisfeld et al. | |
| 2004/0241677 A1 | 12/2004 | Lin et al. | |

FOREIGN PATENT DOCUMENTS

| | | |
|---|---|---|
| WO | WO98/50777 | 11/1998 |
| WO | WO2008/010761 A1 | 1/2008 |

OTHER PUBLICATIONS

PI News/Press Release for NEXACT®: Novel Compact OEM Piezo Stepping Motor/Actuator with Long Travel Range; Aug. 2007; http://www.physikinstrumente.com/en/news/fullnews.php?newsid=123&Wiki_iw.

* cited by examiner

*Primary Examiner* — Tu Nguyen
(74) *Attorney, Agent, or Firm* — Buchanan Ingersoll & Rooney PC (57) ABSTRACT

The invention relates to methods for analysis of particles in a liquid sample, the sample being retained in a sample retaining device, the method comprising: acquiring, by means of an image acquiring device, a plurality of images of said sample at different focus planes within the sample retaining device; analysing said images, by means of an image analyser, for identifying which, if any, of the particles of the sample are imaged in focus in each of the images, and analysing those particles which have been identified as being imaged in focus; wherein said plurality of images are acquired at different, essentially parallel, focus planes, which planes are separated from each other by a distance, said distance being less than 10 micrometers. The invention also relates to apparatuses adapted to be used for the inventive methods.

34 Claims, 3 Drawing Sheets

METHOD AND APPARATUS FOR ANALYSIS OF PARTICLES IN A LIQUID SAMPLE

TECHNICAL FIELD

The present invention relates to a method and an apparatus for image analysis of particles in a liquid sample retained in a sample retaining device.

BACKGROUND OF THE INVENTION

Analysing particles in a liquid sample, e.g. determining the concentration and type of the particles, is of great importance in many different areas of industry, such as agriculture, medicine, etc.

The traditional way of studying particles in a liquid sample is visually, possibly with the aid of a microscope if the particles are small. The particle concentration is normally obtained through a manual procedure by microscopically viewing the sample in a special counting chamber, e.g. a Burker chamber. The counting chamber is provided with a grid dividing the chamber in well-defined small volumes. The particles may be allowed to settle at the bottom of the counting chamber in order to enable the microscope to focus on all particles in the chamber and, thus, facilitate counting. Thus, the sample needs to settle for several minutes before the counting may be performed. The particle count can then be determined by counting the number of particles per box in the grid. The particle count is obtained manually by an analyst, who needs to be experienced in performing the analysis in order to be able to perform a reliable analysis.

This analysis is time-consuming. Further, since it is performed manually, the results of the analysis may vary depending on the person performing the analysis. The analysis is also inaccurate since relatively few particles are counted and the volumes of existing counting chambers are often imprecise.

There are a few existing automated analysis methods for determining particle concentrations in liquid samples. Particle concentrations and sizes, especially for biological particles, such as cells, may be determined by means of the Coulter principle, which is based on sensing an impedance. A method for counting white blood cells by the Coulter principle is described in U.S. Pat. No. 5,262,302. A measurement apparatus according to the Coulter principle is expensive and it is therefore a considerable investment. Thus, a hospital or laboratory will be reluctant to invest in more than one apparatus. This implies that the analysis will need to be performed in a centralised location and a patient will need to wait for analysis results.

In WO 98/50777, a method for assessment of the number of somatic cells in milk is disclosed. The method comprises applying a volume of a sample in a sample compartment and transmitting electromagnetic signals, having passed from the sample compartment, onto an array of detection elements. The intensities of detected electromagnetic signals are processed and the results are correlated to the number of cells present in the sample.

The international application WO 2008/010761 discloses an apparatus and a method for enumeration and typing of particles in a sample. The method comprises the steps of acquiring at least one magnified digital image of the sample, identifying particles which are imaged in focus in the image and determining the types and numbers of these particles. When animal cells are the particles, the optical phenomena at the edges of the cells resulting from the cytoplasm and cell membrane acting as a lens are used to identify which cells are imaged in focus. It is also disclosed that images may be acquired at different focus planes in the sample. It is, however, not mentioned how far apart these focus planes should be.

It is still desired to speed up and simplify existing automated methods for analysis of particles in a liquid sample, e.g. a biological sample. It would be particularly advantageous to provide a quick, simple and relatively inexpensive analysis method such that the analysis may be provided at a point of care.

SUMMARY OF THE INVENTION

It is an object of the invention to provide a simple analysis enabling determination of a volumetric enumeration of particles, such as white blood cells, platelets or bacteria in a sample, such as a blood sample, and identification of the different particles.

Thus, there is, according to an aspect of the present invention, provided a method for analysis of particles in a liquid sample, the sample being retained in a sample retaining device, the method comprising: acquiring, by means of an image acquiring device, a plurality of images of said sample at different focus planes within the sample retaining device; and analysing said images, by means of an image analyser, for identifying particles of the sample which are imaged in focus in any one of the analysed images, and for identifying, for each of the identified particles, in which of said analysed images the particle is identified and analysing those particles which have been identified as being imaged in focus in any one of the analysed images using respective image in which respective particle has been identified as being imaged in focus; wherein said plurality of images are acquired at different, essentially parallel, focus planes, which planes are separated from each other by a distance, said distance being less than 10 micrometers; wherein said identification of particles which are imaged in focus is achieved by, for each of the particles: finding an image in which the particle is distinguishable; determining the greatest difference in light intensity between an area of the image which is occupied by the particle and an area of the image where no particle is distinguishable; determining the corresponding differences in light intensity in other images in which the same particle is distinguishable; and identifying the image where the difference in light intensity is the highest; whereby the particle is regarded as being in focus in that identified image.

By acquiring a plurality of images at different focus planes, a larger volume of the sample can be covered, where the particles are still imaged in focus. Thus also a larger sample retaining device may be used, where the sample depth, perpendicular to the focus planes, may be increased. If the analysis includes a concentration determination, this may be achieved also for particles of a lower concentration, since the volume being analysed is increased.

There is no need to wait for the sample to settle before the images are acquired. The sample may be imaged with the particles in suspension.

By acquiring a plurality of images at different focus planes and determining which particles are imaged in focus in which image, it is also possible to determine how deep down in the sample each of the particles are. It is thus, e.g., possible to separate two or more overlapping particles from each other since they are present at different depths in the sample.

Also, by acquiring a plurality of images at different focus planes and determining which particles are imaged in focus in which image it may be possible to determine the particles dimensions perpendicular to the focus plane, since it will be possible to count in how many images, taken at different but adjacent focus planes, each particle is in focus. However, this is of course dependent on the particles being sufficiently large in relation to the distance between the focus planes.

A smaller distance between the focus planes implies that particles may be imaged in better focus, even at higher magnification. Thus, also smaller particles may be imaged for analysis when the distance between the focus planes is decreased. Also, the particles may be imaged and analysed in higher detail as the advantages of acquiring a plurality of images at different focus planes, discussed above, are amplified with decreasing distance.

Shifting from one focus plane to another may be achieved e.g. by moving a lens, or other light refractor, positioned between the sample and the image acquiring device. In order to shift the focus plane such a small distance as in accordance with the present invention, e.g., a piezoelectric motor might be used for moving the lens. Such a motor also has the advantages of being able to move the lens quickly and with high precision.

The focus planes are essentially parallel to each other and perpendicular to an optical axis, the axis extending from the image acquiring device and through the sample.

The image analyser analyses the plurality of images such that particles, such as cells, that are imaged in focus are identified. This allows an image to be acquired of a relatively thick sample, while only the particles that are in focus are counted or otherwise analysed. By ensuring that only particles that are in focus are counted, i.e. when the particles are imaged in sufficiently clear detail, the identification of the types of particles may be performed in a sample that may simultaneously be used for determining a statistically reliable volumetric enumeration of the particles in the sample.

The advantages of reducing the distance between the focus planes are amplified by reducing the distance even further. Thus the distance is preferably less than 5 micrometers, more preferably less than 2 micrometers, especially 1.8 micrometers or less, specifically 1.6 micrometers or less.

When identifying which particles are imaged in focus in which images, the different images acquired at different focus planes are preferably compared with each other. A specific particle will typically be distinguishable in several different images having different focus planes, where the focus planes of said images are adjacent to each other (i.e. are separated by a distance of less than 10 micrometers). In order to identify in which image this specific particle is imaged in best focus, the contrast of the respective images may be used as a selection criterion. Thus, the greatest difference in light intensity between an area of an image occupied by the specific particle, and an area of the image were no particle is distinguishable, i.e. background, is determined. Other images where the same particle is distinguishable are studied in the same way. Thus, the image displaying the greatest contrast with respect to the specific particle can be identified and the particle is regarded as being in focus in this identified image. The same procedure may then be repeated for all particles distinguishable in any of the acquired images.

Also, as a complement or alternative, identifying which particles are imaged in focus in which of the acquired images may be done based on the pixel, or sample, variance. The pixel variance may be biased ($s^2_N$) or bias-corrected ($s^2_{N-1}$). The bias-corrected pixel variance is calculated according to the following formula:

$$s^2_{N-1} \equiv \frac{1}{N-1} \sum_{i=1}^{N} (x_i - \bar{x})^2$$

wherein N is the number of pixels, x is the light intensity of pixel i, and $\bar{x}$ is the mean light intensity.

When using the pixel variance for identifying in which of the acquired images a particle is imaged in focus, an area comprising the particle, as well as the particle's closest surroundings (background), is defined. The pixel variance is then determined for that defined area. The pixel variance is also determined for the corresponding area of the other acquired images. The image which is identified as having the highest pixel variance is the image in which the particle is regarded as being in focus. The procedure may then be repeated for other particles which are distinguishable in any of the acquired images.

Thus, there is, according to an aspect of the present invention, also provided a method for analysis of particles in a liquid sample, the sample being retained in a sample retaining device, the method comprising: acquiring, by means of an image acquiring device, a plurality of images of said sample at different focus planes within the sample retaining device; and analysing said images, by means of an image analyser, for identifying particles of the sample which are imaged in focus in any one of the analysed images, and for identifying, for each of the identified particles, in which of said analysed images the particle is identified and analysing those particles which have been identified as being imaged in focus in any one of the analysed images using respective image in which respective particle has been identified as being imaged in focus; wherein said plurality of images are acquired at different, essentially parallel, focus planes, which planes are separated from each other by a distance, said distance being less than 10 micrometers; wherein said identification of particles which are imaged in focus is achieved by, for each of the particles: finding an image in which the particle is distinguishable; defining an area of that found image, said area comprising the particle and its closest surroundings; determining the pixel variance of that defined area; determining the pixel variance of the corresponding area of other images in which the same particle is distinguishable; and identifying the image where the pixel variance is the highest; whereby the particle is regarded as being in focus in that identified image.

The discussion above relating to the inventive method which includes determining differences in light intensities is also in applicable parts relevant to the inventive method which includes determining pixel variances. Reference is made to that discussion. The discussion below relates to optional features of both inventive methods.

The specific particle may be identified as being the same particle in the plurality of images by having essentially the same spatial position in each of the images where said particle is distinguishable, since the images are acquired with different focus planes along an optical axis from the image acquiring device through the sample, but are not shifted sideways. Thus, the images are essentially of the same area of the sample, but at different depths in said sample. Since the particles are in a liquid sample, and thus might move slightly over time, it is desirable to acquire the images over a relatively short time. Preferably at least two images, more preferably at least 5 images, and most preferably at least 10 images, are acquired per second. This also speeds up the analysis as a whole.

Any of the inventive methods may further comprise superpositioning the plurality of images, thereby obtaining a superpositioned image containing all the particles imaged in focus at the different focus planes. Thus, the whole analysed volume of the sample may be represented in a single two-dimensional image where the particles of the sample may be displayed in focus, regardless of how deep down in the sample volume each of them really were when being imaged.

Preferably, the plurality of images are acquired in a sequence of only one image per focus plane where the focus plane is moved a specific distance, less than 10 micrometers, between each image. This way of acquiring the images is quick and may be accomplished by means of a simple apparatus.

A larger volume of the sample may be covered if a larger amount of images are acquired. As mentioned above, the larger the volume, the more accurate e.g. a concentration determination may be, and also particles of a lower concentration may be concentration determined. Conveniently at least 10, preferably at least 20, more preferably at least 50, even more preferably at least 100, and most preferably at least 200, images are acquired in accordance with the present invention.

Also, in order to be able to analyse a large volume of the sample, the sample retaining device may be able to present the liquid sample for imaging such that the sample has a depth, perpendicular to the focus planes, which is sufficiently large. Said depth is preferably at least 100 micrometers, more preferably at least 200 micrometers and even more preferably at least 500 micrometers.

Conveniently, the sample retaining device is arranged to present the sample for imaging such that the depth of the sample is 1 millimetre or less. This implies that the sample retaining device may have a chamber which has a dimension which is 1 millimetre or less, whereby a liquid sample could be introduced into the chamber through capillary action. The liquid sample could thus be sucked directly into the chamber through an inlet, communicating the chamber with the outside of the device, eliminating the need for pipettes, pumps or such equipment. More specifically, blood could even be sucked into the chamber directly from the pricked finger of a patient. Of course, the other dimensions of the chamber may be larger, and, depending on how large area of the sample is being imaged by the image acquiring device, it might indeed be desired that the other dimensions are larger.

The present invention is particularly interesting for biological analyses. The liquid sample may thus be a biological sample, such as milk, urine, spinal fluid or, particularly, blood, e.g. whole blood or plasma.

The particles may also be biological, such as eukaryotic cells, preferably mammalian cells, more preferably human cells such as human white blood cells. However, since even smaller particles may be sufficiently analysed in accordance with the present invention because the distance between the different focus planes is so small, the particles may, as an alternative, have a maximum diameter of less than 20, conveniently less than 10, preferably less than 5, and more preferably less than 2, micrometers. Examples of such small biological particles which are of great interest for analysis by means of the present invention are e.g. bacteria, viruses and platelets.

As mentioned above, as an example of an analysis, the method of the invention may be used for determining the concentration of particles in the sample. The number of identified particles are then put in relation to the volume of the sample which is imaged. This volume is defined by the imaged area of the sample multiplied with the imaged depth of the sample. The imaged area is determined by the choice of image acquiring device, in combination with any magnification or reduction. The imaged depth is a function of the number of images and the distance between each image. This analysis may of course be dependent on the distance being sufficiently small, or the particles being large enough, for all particles, to be enumerated in the imaged volume, to be imaged in focus in at least one of the images. Another analysis which may be enabled by the present invention is determining the different types of particles. The different types of particles may be determined by their respective physical features. Such features may e.g. be the size, colour, opalescence and/or shape of the particles. Preferably, the analysis of the particles in accordance with the present invention includes determining the types and quantities of the particles such that the ratios of different types of particles in the sample may be determined. The analysing of those particles which have been identified as being imaged in focus may thus comprise determining the types and quantities of the particles, the types being distinguished by physical features of the particles, whereby the ratios of different types of particles in the sample are determined.

The particles to be analysed may have been stained by means of a staining agent prior to the images being acquired. This implies that the particles may be more easily distinguishable from the background liquid. If e.g. the particles are eukaryotic cells, a staining agent selectively staining the cell nuclei may be employed. In order to further improve the distinguishability in the acquired images, the sample may then be irradiated with light of a specific wavelength which is absorbed by the staining agent, whereby the cell nuclei will be clearly imaged as dark areas or dots against a lighter background. Alternatively, the staining agent may e.g. be a fluorescent dye, or a fluorescently marked antibody, or antibody fragment, which bind specifically to the particles to be analysed. The sample may then be irradiated with an electromagnetic wavelength which is absorbed by the fluorophore of the dye or antibody, and the image acquiring device may be adapted to specifically detect the electromagnetic wavelength subsequently emitted by the fluorophore, whereby the stained particles will be imaged as light areas or dots against a darker background.

The staining agent may be present in a dried form within the sample retaining device prior to the liquid sample being introduced into the sample retaining device. Thus, the staining agent may be included in the sample retaining device during its production. The staining agent may e.g. be dried onto a wall of a chamber of the device, into which chamber the liquid sample is later introduced, dissolving the staining agent, prior to images being acquired of the sample in the chamber of the sample retaining device according to the present invention. Also other reagents or chemical agents may be included in the sample retaining device, instead of, or in addition to, a staining agent, such as a haemolysing agent, for lysing red blood cells in a sample of whole blood, or a wetting agent, e.g. for facilitating the liquid sample being sucked into the sample retaining device by capillary action. By including all the chemical agents needed for an analysis by the inventive method, the sample retaining device provides a possibility to directly obtain a sample into a chamber of the device and provide it for analysis. There is no need for sample preparation. In fact, if the chamber is capillary as discussed above, a blood sample may be sucked into the chamber directly from a pricked finger of a patient, or any sample may be sucked into the chamber directly from a tube or well or any other type of container. Providing the sample retaining device with a reagent enables a reaction within the sample retaining device which makes the sample ready for analysis. The reaction is initiated when the sample comes into contact with the reagent. Thus, there is no need for manually preparing the sample, which makes the analysis especially suitable to be performed directly in an examination room e.g. while a patient is waiting.

Since the reagent is provided in a dried form, the sample retaining device may be a ready-to-use kit which may be transported and stored for a long time without affecting the usability of the sample retaining device. Thus, the sample retaining device with the reagent may be manufactured and prepared long before making the analysis of a sample.

The sample retaining device may be disposable, i.e. it is arranged to be used only once. If the sample retaining device is adapted for use only once, it may be formed without consideration of any possibility to clean the sample retaining device and possibly re-apply a reagent. Also, the sample retaining device may be moulded in a plastic material and thereby be manufactured at a low cost. Thus, it may still be cost-effective to use a disposable sample retaining device.

The image acquiring device may be a digital camera. Such an image acquiring device allows the entire area of an image to be acquired to be imaged simultaneously, after which the image may be directly presented to the image analyser for digital image analysis. The camera may e.g. be of CCD or CMOS type.

Depending on e.g. the sizes of the particles imaged and the resolution of the image acquiring device, it may be advantageous to acquire the images either of a magnification or a reduction of the liquid sample. The magnification or reduction may be achieved by means of a light refractor, such as a lens, which is positioned such that it intersects the optical axis between the sample and the image acquiring device. Conveniently, a magnification is used, such as a magnification of 2-50×, preferably 2-30×, more preferably 2-20×, most preferably 3-10×. However, if very small particles, such as bacteria, viruses or platelets, are to be analysed, even higher magnification might be preferred; such as 10-50×, more preferably 10-35×, most preferably 10-20×. Even though a high magnification is used, a sufficiently large volume may still be covered by the images since many images are acquired at different focus planes in the sample. An imaged volume of the sample may thus be defined by an imaged area of the sample multiplied with a depth of the sample covered by the plurality of images.

As mentioned above, the optical magnification, or reduction, used is linked to the resolution of the image acquiring device. That resolution is conveniently at least 3 Mpixel, preferably at least 5 Mpixel, specifically 6 Mpixel or more.

According to another aspect of the present invention, there is provided a measurement apparatus for analysis of particles in a liquid sample, the apparatus comprising an image acquiring device, an image analyser, a holder arranged to hold a sample retaining device retaining the liquid sample, and a light refractor positioned between said image acquiring device and said holder; wherein a focus plane is movable stepwise within the sample retaining device when it is held by the holder, whereby the image acquiring device is adapted to acquire a plurality of images of said sample at different focus planes within the sample retaining device, the different focus planes being essentially parallel to each other and being separated from each other by a distance, said distance being less than 10 micrometers; wherein the image analyser is arranged to analyse at least one acquired image for identifying which of the particles are imaged in focus, and analysing those particles which have been identified as being imaged in focus; wherein said identification of particles which are imaged in focus is achieved by, for each of the particles: finding an image in which the particle is distinguishable; determining the greatest difference in light intensity between an area of the image which is occupied by the particle and an area of the image where no particle is distinguishable; determining the corresponding differences in light intensity in other images in which the same particle is distinguishable; and identifying the image where the difference in light intensity is the highest; whereby the particle is regarded as being in focus in that identified image.

Alternatively, the present invention provides a measurement apparatus for analysis of particles in a liquid sample, the apparatus comprising an image acquiring device, an image analyser, a holder arranged to hold a sample retaining device retaining the liquid sample, and a light refractor positioned between said image acquiring device and said holder; wherein a focus plane is movable stepwise within the sample retaining device when it is held by the holder, whereby the image acquiring device is adapted to acquire a plurality of images of said sample at different focus planes within the sample retaining device, the different focus planes being essentially parallel to each other and being separated from each other by a distance, said distance being less than 10 micrometers; wherein the image analyser is arranged to analyse at least one acquired image for identifying which of the particles are imaged in focus, and analysing those particles which have been identified as being imaged in focus; wherein said identification of particles which are imaged in focus is achieved by, for each of the particles: finding an image in which the particle is distinguishable; defining an area of that found image, said area comprising the particle and its closest surroundings; determining the pixel variance of that defined area; determining the pixel variance of the corresponding area of other images in which the same particle is distinguishable; and identifying the image where the pixel variance is the highest; whereby the particle is regarded as being in focus in that identified image.

The discussion below relates to both alternative measurement apparatuses.

The apparatus comprises a holder, which is arranged to receive a sample retaining device, described above in respect of the inventive method, that holds the liquid sample of which images are acquired in accordance with the present invention.

The focus plane may be moved stepwise through the liquid sample along the optical axis of the apparatus, said axis running from the image acquiring device and through the holder, such that each step is less than 10 micrometers, allowing an image to be acquired after each step.

The focus plane may be moved e.g. by moving the light refractor, e.g. a lens, along the optical axis of the apparatus while the holder and the image acquiring device remains still. For moving the focus plane such a small distance as in accordance with the present invention as well as sufficiently fast and with sufficient precision, reproducibility and stability, it is preferred to use a piezoelectric motor to move the light refractor.

Any of the apparatuses may further comprise an electromagnetic radiation source, which is arranged to irradiate the sample retained in the sample retaining device. Any conventional radiation source may be used, such as a light emitting diode, a laser or a glow lamp. The light source allows the particles of the sample to be more easily distinguishable in the images. If it is desirable to irradiate the sample with a specific wavelength, this may be achieved by conventional means, such as by employing a laser, or a chromatic filter in combination with the light source.

The discussion above relating to the inventive methods is also in applicable parts relevant to the inventive apparatuses. Reference is made to that discussion.

The apparatuses and methods of the invention provide, from a users perspective, a very simple analysis of a liquid sample, such as whole blood. The analysis does not require complicated measurement apparatus or advanced steps to be performed by an operator. Therefore, it may be performed in direct connection to e.g. the examination of a patient, without the need for a qualified technician. It is merely required that the sample to be analysed is introduced into, and retained by, the sample retaining device. Then, the sample may be analysed according to the inventive method, preferably by the inventive apparatus in an automated fashion and, in direct response thereto, the apparatus may present the analysis results.

BRIEF DESCRIPTION OF THE DRAWINGS

The invention will now be described in further detail by way of example under reference to the accompanying drawings.

DETAILED DESCRIPTION OF PREFERRED EMBODIMENTS

Figure 1:
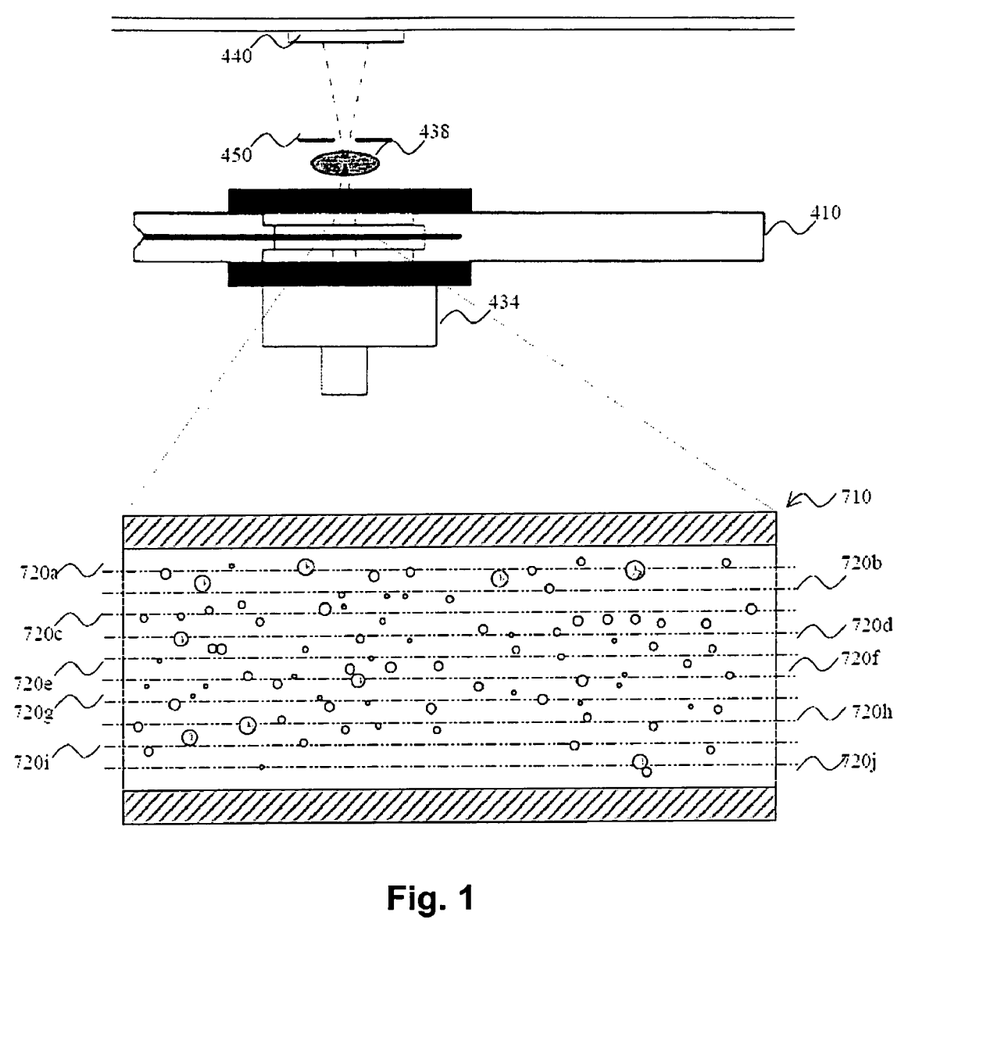
FIG. 1 is a schematic view of an apparatus according to the invention.

With reference to FIG. 1, an apparatus of the present invention comprises a light source 434, a sample retaining device 410, an optical system 438 (with a magnification factor of 5×, an image acquiring device with a resolution of 6 Mpixel, and an ability to move the focus plane), and a diaphragm 450 directing the light to an image acquiring device 440. The apparatus is arranged to acquire several digital images of the sample using different optical settings. For example, the several digital images may image ten different layers 720*a-j* of the sample 710.

Figure 2:
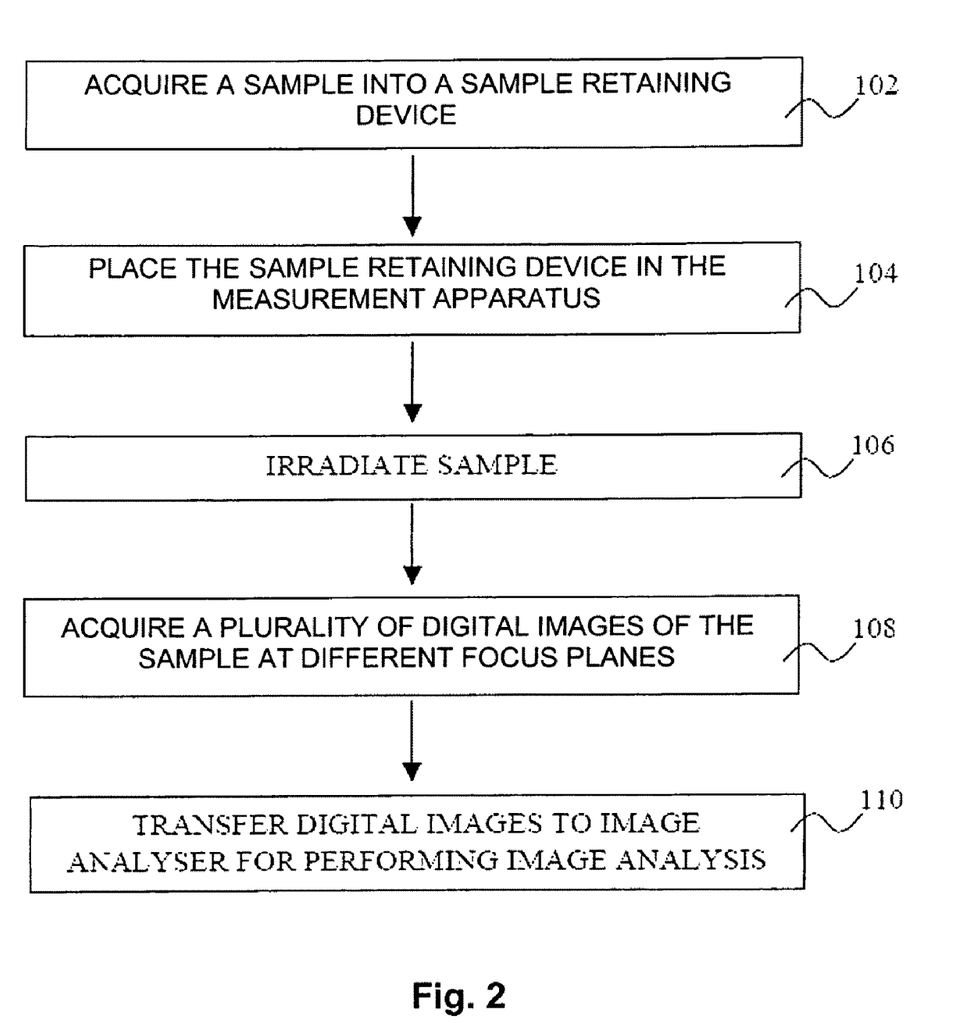
FIG. 2 is a flow chart of a method according to the invention.

With reference to FIG. 2, a method for volumetric enumeration of white blood cells will be described. The method comprises acquiring a blood sample into a sample retaining device, step 102. An undiluted sample of whole blood is acquired into the sample retaining device. The sample may be acquired from capillary blood or venous blood. A sample of capillary blood may be drawn into a chamber of the sample retaining device directly from a pricked finger of a patient. The blood sample makes contact with a dried reagent, comprising a haemolysing agent and a staining agent, within the sample retaining device, initiating a reaction. The red blood cells will be lysed and the staining agent is accumulated in the nuclei of the white blood cells of the sample. Within a few minutes from acquiring the blood sample, the sample is ready to be analysed. Alternatively, a blood sample is acquired and mixed with a haemolysing agent and a staining agent before being introduced into the sample retaining device. The sample retaining device is then placed in an apparatus of the invention, step 104. An analysis may be initiated by pushing a button of the apparatus. Alternatively, the analysis is automatically initiated by the apparatus detecting the presence of the sample retaining device.

The sample is irradiated, step 106, and a plurality of digital images, with a resolution of 6 Mpixel, are acquired at different layers of the sample, i.e. at different focus planes, at a distance of 1.6 micrometers from each other and with an optical magnification of 5×, step 108. The sample is being irradiated with electromagnetic radiation of a wavelength corresponding to an absorption peak of the staining agent. This implies that the digital images will contain black or darker dots in the positions of the white blood cell nuclei.

The acquired digital images are transferred to an image analyser, which performs image analysis of the plurality of digital images, step 110. The image analyser determines the concentration of white blood cells by counting black dots, identifies which cells are in focus in which image and analyses the size and shape of a certain number of the cells in focus in order to classify the white blood cells and obtain a ratio of different types of white blood cells in the blood sample.

Figure 3:
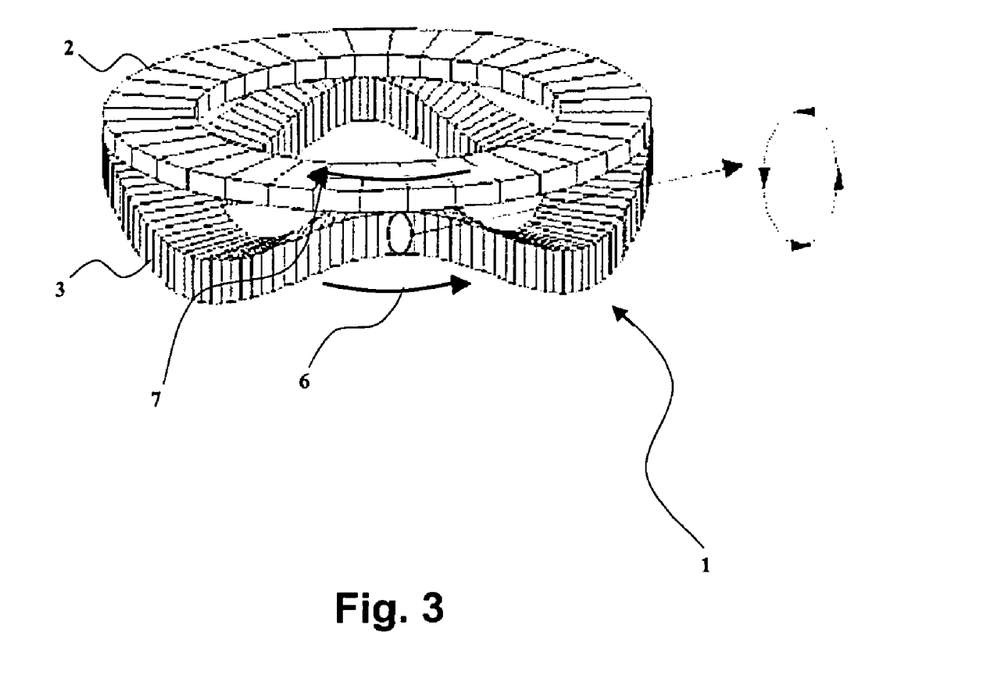
FIG. 3 is a schematic perspective view of a piezo electric motor which may be used in preferred embodiments of the inventive method or apparatus.

With reference to FIG. 3, a piezoelectric motor 1 comprises a circular shaped stator 3 and a circular shaped rotor 2, which rotor 2 is pressed onto the surface of the stator 3, thereby enabling a mechanical output. During operation of the motor a travelling wave is generated over the surface of the stator 3, in a direction indicated by the arrow 6, said surface behaves as a flexible ring, and produces elliptical motion at the rotor interface. This elliptical motion of the contact surface propels the rotor 2 in a direction indicated by the arrow 7, and thereby enabling motion of a drive shaft connected to it. The directions indicated by the arrow 6 and the arrow 7 may, as is easily realised, be the reversed of what is indicated in FIG. 3. Teeth attached to the stator 3 may be used to increase the rotational speed. The out-put from the motor is dependent on, for example, the friction at the interface between the moving rotor and the stator, and the amplitude and other characteristics of the travelling wave in the stator 3.

It should be emphasized that the preferred embodiments described herein are in no way limiting and that many alternative embodiments are possible within the scope of protection defined by the appended claims.

What is claimed is:

1. A method for analysis of particles in a liquid sample, the sample being retained in a sample retaining device, the method comprising:

acquiring, by means of an image acquiring device, a plurality of images of said sample at different focus planes within the sample retaining device; and analysing said images, by means of an image analyser, for identifying particles of the sample which are imaged in focus in any one of the analysed images, and for identifying, for each of the identified particles, in which of said analysed images the particle is identified and analysing those particles which have been identified as being imaged in focus in any one of the analysed images using respective image in which respective particle has been identified as being imaged in focus;

wherein said plurality of images are acquired at different, essentially parallel, focus planes, which planes are separated from each other by a distance, said distance being less than 10 micrometers;

wherein said identification of particles which are imaged in focus is achieved by, for each of the particles:

finding an image in which the particle is distinguishable;

determining the greatest difference in light intensity between an area of the image which is occupied by the particle and an area of the image where no particle is distinguishable;

determining the corresponding differences in light intensity in other images in which the same particle is distinguishable; and identifying the image where the difference in light intensity is the highest;
whereby the particle is regarded as being in focus in that identified image.

2. The method of claim 1, wherein the distance is less than 5 micrometers.

3. The method of claim 1, wherein the distance is less than 2 micrometers.

4. The method of claim 1, wherein the method further comprises superpositioning the plurality of images, thereby obtaining a superpositioned image containing all the particles imaged in focus at the different focus planes.

5. The method of claim 1, wherein only one image per focus plane is acquired.

6. The method of claim 1, wherein at least 10 images are acquired.

7. The method of claim 1, wherein at least 100 images are acquired.

8. The method of claim 1, wherein at least 200 images are acquired.

9. The method of claim 1, wherein the sample retaining device is arranged to present the liquid sample for imaging such that the sample has a depth, perpendicular to the focus planes, of at least 100 micrometers.

10. The method of claim 1, wherein the sample retaining device is arranged to present the liquid sample for imaging such that the sample has a depth, perpendicular to the focus planes, of at least 200 micrometers.

11. The method of claim 1, wherein the sample retaining device is arranged to present the liquid sample for imaging such that the sample has a depth, perpendicular to the focus planes, of at least 500 micrometers.

12. The method of claim 1, wherein the sample retaining device is arranged to present the liquid sample for imaging such that the sample has a depth, perpendicular to the focus planes, of 1 millimeter or less.

13. The method of claim 1, wherein the liquid sample is a biological sample.

14. The method of claim 1, wherein the liquid sample is a blood sample.

15. The method of claim 1, wherein the particles are eukaryotic cells.

16. The method of claim 1, wherein the particles are mammalian cells.

17. The method of claim 1, wherein the particles are human cells.

18. The method of claim 1, wherein the particles are bacteria, viruses or platelets.

19. The method of claim 1, wherein the particles have a maximum diameter of less than 20 micrometers.

20. The method of claim 1, wherein the particles have a maximum diameter of less than 10 micrometers.

21. The method of claim 1, wherein the particles have a maximum diameter of less than 2 micrometers.

22. The method of claim 1, wherein the analysing of those particles which have been identified as being imaged in focus comprises determining the types and quantities of the particles, the types being distinguished by physical features of the particles, whereby the ratios of different types of particles in the sample are determined.

23. The method of claim 1, wherein the particles to be analysed have been stained, by means of a staining agent, prior to the images being acquired.

24. The method of claim 23, wherein the liquid sample is contacted with the staining agent, the staining agent being in a dry form, within the sample retaining device, whereby the staining agent is dissolved in the sample.

25. The method of claim 23, wherein the staining agent is a fluorescent staining agent.

26. The method of claim 1, wherein the image acquiring device is a digital camera.

27. The method of claim 1, wherein the images, acquired by means of the image acquiring device, are acquired of a magnification of the liquid sample, said magnification being achieved by means of a light refractor.

28. The method of claim 1, wherein the images, acquired by means of the image acquiring device, are acquired of a magnification of the liquid sample, said magnification being achieved by means of a lens.

29. The method of claim 1, wherein an imaged volume of the sample is defined by an imaged area of the sample multiplied with a depth of the sample covered by the plurality of images.

30. A method for analysis of particles in a liquid sample, the sample being retained in a sample retaining device, the method comprising:
  acquiring, by means of an image acquiring device, a plurality of images of said sample at different focus planes within the sample retaining device; and
  analysing said images, by means of an image analyser, for identifying particles of the sample which are imaged in focus in any one of the analysed images, and for identifying, for each of the identified particles, in which of said analysed images the particle is identified and analysing those particles which have been identified as being imaged in focus in any one of the analysed images using respective image in which respective particle has been identified as being imaged in focus;
  wherein said plurality of images are acquired at different, essentially parallel, focus planes, which planes are separated from each other by a distance, said distance being less than 10 micrometers;
  wherein said identification of particles which are imaged in focus is achieved by, for each of the particles:
  finding an image in which the particle is distinguishable;
  defining an area of that found image, said area comprising the particle and its closest surroundings;
  determining the pixel variance of that defined area;
  determining the pixel variance of the corresponding area of other images in which the same particle is distinguishable; and
  identifying the image where the pixel variance is the highest;
  whereby the particle is regarded as being in focus in that identified image.

31. A measurement apparatus for analysis of particles in a liquid sample, the apparatus comprising an image acquiring device, an image analyser, a holder arranged to hold a sample retaining device retaining the liquid sample, and a light refractor positioned between said image acquiring device and said holder;
  wherein a focus plane is movable stepwise within the sample retaining device when it is held by the holder, whereby the image acquiring device is adapted to acquire a plurality of images of said sample at different focus planes within the sample retaining device, the different focus planes being essentially parallel to each other and being separated from each other by a distance, said distance being less than 10 micrometers;
  wherein the image analyser is arranged to analyse at least one acquired image for identifying which of the particles are imaged in focus and analysing those particles which have been identified as being imaged in focus;

wherein said identification of particles which are imaged in focus is achieved by, for each of the particles:

finding an image in which the particle is distinguishable;

determining the greatest difference in light intensity between an area of the image which is occupied by the particle and an area of the image where no particle is distinguishable;

determining the corresponding differences in light intensity in other images in which the same particle is distinguishable; and identifying the image where the difference in light intensity is the highest;

whereby the particle is regarded as being in focus in that identified image.

32. The apparatus of claim 31, wherein the distance is less than 5 micrometers.

33. The apparatus of claim 31, wherein the distance is less than 2 micrometers.

34. A measurement apparatus for analysis of particles in a liquid sample, the apparatus comprising an image acquiring device, an image analyser, a holder arranged to hold a sample retaining device retaining the liquid sample, and a light refractor positioned between said image acquiring device and said holder;

wherein a focus plane is movable stepwise within the sample retaining device when it is held by the holder, whereby the image acquiring device is adapted to acquire a plurality of images of said sample at different focus planes within the sample retaining device, the different focus planes being essentially parallel to each other and being separated from each other by a distance, said distance being less than 10 micrometers;

wherein the image analyser is arranged to analyse at least one acquired image for identifying which of the particles are imaged in focus, and analysing those particles which have been identified as being imaged in focus;

wherein said identification of particles which are imaged in focus is achieved by, for each of the particles:

finding an image in which the particle is distinguishable;

defining an area of that found image, said area comprising the particle and its closest surroundings;

determining the pixel variance of that defined area;

determining the pixel variance of the corresponding area of other images in which the same particle is distinguishable; and identifying the image where the pixel variance is the highest;

whereby the particle is regarded as being in focus in that identified image.

\* \* \* \* \*